United States Patent
Göres et al.

(10) Patent No.: US 6,552,210 B1
(45) Date of Patent: Apr. 22, 2003

(54) TRANSITION METAL COMPOUND CONTAINING CATIONIC GROUPS WHICH IS USED AS AN OLEFIN POLYMERIZATION CATALYST COMPONENT

(75) Inventors: Markus Göres, Eschborn (DE); Hans Bohnen, Moers (DE)

(73) Assignee: Targor GmbH, Mainz (DE)

( * ) Notice: Subject to any disclaimer, the term of this patent is extended or adjusted under 35 U.S.C. 154(b) by 0 days.

(21) Appl. No.: 09/623,654

(22) PCT Filed: Mar. 17, 1999

(86) PCT No.: PCT/EP99/01732

§ 371 (c)(1), (2), (4) Date: Sep. 7, 2000

(87) PCT Pub. No.: WO99/50274

PCT Pub. Date: Oct. 7, 1999

(30) Foreign Application Priority Data

Mar. 27, 1998 (DE) .......... 198 13 656

(51) Int. Cl.⁷ .......... C07F 17/00
(52) U.S. Cl. .......... 556/53; 526/127; 526/128; 526/129; 526/351
(58) Field of Search .......... 572/53; 526/127, 526/128, 129, 351

(56) References Cited

U.S. PATENT DOCUMENTS

| 5,627,246 A | 5/1997 | Langhauser |
| 5,770,753 A | 6/1998 | Kueber |
| 5,786,432 A | 7/1998 | Kueber |
| 5,840,644 A | 11/1998 | Kueber |

FOREIGN PATENT DOCUMENTS

| EP | 576 970 | 1/1994 |
| EP | 670 336 | 9/1995 |

OTHER PUBLICATIONS

Chem.Lttrs. 2047–2050, 1991, Tani et al.
J.Org.Chem., 288(1985) 63–67, Wild et al.

*Primary Examiner*—Paul F. Shaver
(74) *Attorney, Agent, or Firm*—Keil & Weinkauf

(57) ABSTRACT

Specifically substituted metallocenes can be used in the polymerization of olefins. The novel compounds contain a cationic group as substituents and are suitable as constituents of a catalyst system for the polymerization of olefins.

8 Claims, No Drawings

TRANSITION METAL COMPOUND CONTAINING CATIONIC GROUPS WHICH IS USED AS AN OLEFIN POLYMERIZATION CATALYST COMPONENT

The present invention relates to specifically substituted metallocenes, a process for preparing them and their use in the polymerization of olefins.

Processes for preparing polyolefins with the aid of soluble, homogeneous catalyst systems comprising a transition metal component of the metallocene type and a cocatalyst component such as an aluminoxane, a Lewis acid or an ionic compound are known. These catalysts have a high activity and give polymers and copolymers having a narrow molar mass distribution.

In polymerization processes using soluble, homogeneous catalyst systems, thick deposits are formed on reactor walls and stirrer when the polymer is formed as a solid. These deposits are formed by agglomeration of the polymer particles whenever metallocene and/or cocatalyst are present in dissolved form in the suspension. Such deposits in the reactor systems have to be removed regularly, since they quickly attain considerable thicknesses, have a high strength and prevent heat exchange to the cooling medium. Such homogeneous catalyst systems cannot be used industrially in modern polymerization processes in the liquid monomer or in the gas phase.

To avoid deposit formation in the reactor, supported catalyst systems in which the metallocene and/or the aluminum compound serving as cocatalyst are/is fixed to an inorganic support material have been proposed.

EP-A-0,576,970 A1 discloses metallocenes and corresponding supported catalyst systems.

However, a frequent problem in the industrial use of supported catalyst systems is leaching of the metallocene component from the support material, resulting, for example, in undesirable deposit formation in the reactor.

It is an object of the present invention to find novel metallocenes which can be firmly fixed to a support and are not leached from the support material under industrially relevant polymerization conditions.

We have found that this object is achieved by specifically substituted metallocenes containing a cationic-group as substituent.

The present invention accordingly provides metallocenes of the formula (I),

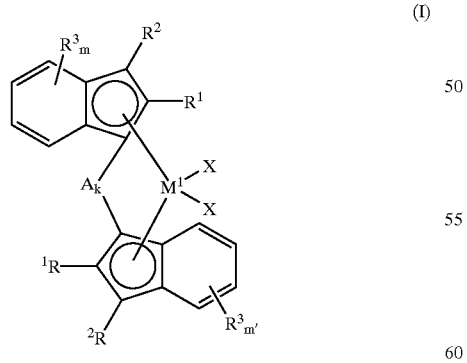

(I)

where

M$^1$ is a transition metal of group 4 of the Periodic Table of the Elements, for example titanium, zirconium or hafnium, preferably zirconium, R$^1$ and R$^2$ are identical or different and are each a hydrogen atom, a C$_1$–C$_{20}$ group, preferably a C$_1$–C$_{20}$-alkyl group, a C$_6$–C$_{14}$-aryl group, a C$_2$–C$_{20}$-alkenyl group, a C$_2$–C$_{20}$-alkynyl group, a C$_7$–C$_{20}$-alkylaryl group, each of which may bear one or more identical or different halogen atoms as substituents, a halogen atom, an —SiMe$_3$ group or an OSiMe$_3$ group; R$^1$ and/or R$^2$ are particularly preferably hydrogen, methyl, ethyl, n-propyl, isopropyl, n-butyl, sec-butyl, isobutyl, tert-butyl, n-pentyl, branched pentyl, n-hexyl, branched hexyl, cyclohexyl or benzyl, R$^3$ are identical or different and are each a hydrogen atom or a C$_1$–C$_{40}$ group, preferably a C$_1$–C$_{20}$-alkyl group which may be substituted, in particular methyl, ethyl, trifluoroethyl, n-propyl, isopropyl, n-butyl, sec-butyl, isobutyl, tert-butyl, pentyl, hexyl, octyl, cyclopropyl, cyclopentyl or cyclohexyl, a C$_6$–C$_{14}$-aryl group which may be substituted, in particular phenyl, tolyl, xylyl, tert-butylphenyl, ethylphenyl, trifluoromethylphenyl, bis(trifluoromethyl)phenyl, methoxyphenyl, fluorophenyl, dimethylaminophenyl, trimethylammoniumphenyl iodide, dimethylsulfoniumphenyl bromide, triethylphosphoniumphenyl triflate, naphthyl, acenaphthyl, phenanthrenyl or anthracenyl, a C$_2$–C$_{20}$-alkenyl group, a C$_2$–C$_{20}$-alkynyl group, a C$_7$–C$_{20}$-alkylaryl group, a halogen atom, an SiMe$_3$ group, an OSiMe$_3$ group, a C$_1$–C$_{20}$-heterocyclic group which may be substituted, where the term heteroatom encompasses all elements with the exception of carbon and hydrogen, preferably atoms of groups 14, 15 or 16 of the Periodic Table of the Elements, and two radicals R$^3$ may form a monocyclic or polycyclic ring system which may in turn be substituted, where at least one of the radicals R$^1$, R$^2$, R$^3$ comprises a cationic group (—DE$_L$)$^+$Y$^-$, where D is an atom of group 15 or 16 of the Periodic Table of the Elements, preferably nitrogen, phosphorus, oxygen or sulfur, E are identical or different and are each a hydrogen atom, a C$_1$–C$_{20}$ group, preferably a C$_1$–C$_{20}$-alkyl group, a C$_6$–C$_{14}$-aryl group, a C$_2$–C$_{20}$-alkenyl group, a C$_2$–C$_{20}$-alkynyl group or a C$_7$–C$_{20}$-alkylaryl group, a trialkylsilyl group, a triarylsilyl group, an alkylarylsilyl group which may be substituted, and two radicals E may form a monocyclic or polycyclic ring system which may in turn be substituted;

E is particularly preferably a hydrogen atom, methyl, ethyl, propyl, butyl, allyl, benzyl, methoxymethyl, benzyloxymethyl, 2-methoxyethoxymethyl, 2-trimethylsilylethoxymethyl, trimethylsilyl;

L is 3 when D is an atom of group 15 of the Periodic Table of the Elements and is 2 when D is an atom of group 16 of the Periodic Table of the Elements, Y is halide, C$_1$–C$_{10}$-alkylsulfonate, C$_1$–C$_{10}$-haloalkylsulfonate, C$_6$–C$_{20}$-arylsulfonate, C$_6$–C$_{20}$-haloarylsulfonate, C$_7$–C$_{20}$-alkylarylsulfonate, C$_1$–C$_{20}$-haloalkylcarboxylate, C$_1$–C$_{10}$-alkyl sulfate, tetrafluoroborate, hexafluorophosphate, hexafluoroantimonate, hexafluoroarsenate; Y is preferably chloride, bromide, iodide, triflate, mesylate, tosylate, benzenesulfonate, trifluoroacetate, methyl sulfate, tetrafluoroborate or hexafluorophosphate;

m is an integer less than or equal to 4 and greater than or equal to 1, preferably 1 or 2, particularly preferably 1, m' is an integer less than or equal to 4 and greater than or equal to 1, preferably 1 or 2, particularly preferably 1, k is zero or 1, where the metallocene is unbridged when k=0 and is bridged when k=1, A is a bridge of the following type

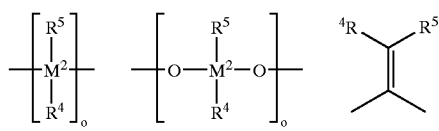

or $=BR^4$, $AlR^4$, —S—, —SO—, —SO$_2$—, $=NR^4$, $=PR^4$, $=P(O)R^4$, o-phenylene, 2,2'-biphenylene, where $M^2$ is carbon, silicon, germanium, tin, nitrogen or phosphorus, preferably carbon, silicon or germanium, in particular carbon or silicon, o is 1, 2, 3 or 4, preferably 1 or 2, $R^4$ and $R^5$ are identical or different and are each a hydrogen atom, halogen, a $C_1$–$C_{20}$ group, preferably $C_1$–$C_{20}$-alkyl, in particular a methyl group, $C_6$–$C_{14}$-aryl, in particular a phenyl or naphthyl group, $C_1$–$C_{10}$-alkoxy, $C_2$–$C_{10}$-alkenyl, $C_7$–$C_{20}$-arylalkyl, $C_7$–$C_{20}$-alkylaryl, $C_6$–$C_{10}$-aryloxy, $C_1$–$C_{10}$-fluoroalkyl, $C_6$–$C_{10}$-haloaryl, $C_2$–$C_{10}$-alkynyl, $C_3$–$C_{20}$-alkylsilyl, in particular trimethylsilyl, triethylsilyl, tert-butyldimethylsilyl, $C_3$–$C_{20}$-arylsilyl, in particular triphenylsilyl, or $C_3$–$C_{20}$-alkylarylsilyl, in particular dimethylphenylsilyl, diphenylsilyl or diphenyl-tert-butylsilyl, and $R^4$ and $R^5$ may form a monocyclic or polycyclic ring system;

A is preferably dimethylsilanediyl, dimethylgermanediyl, ethylidene, methylethylidene, 1,1-dimethylethylidene, 1,2-dimethylethylidene, tetramethylethylidene, isopropylidene, phenylmethylmethylidene, diphenylmethylidene, particularly preferably dimethylsilanediyl or ethylidene;

The radicals X are identical or different and are each a hydrogen atom, a halogen atom such as fluorine, chlorine, bromine or iodine, a hydroxyl group, a $C_1$–$C_{10}$-alkyl group such as methyl, ethyl, propyl, isopropyl, n-butyl, isobutyl, sec-butyl, tert-butyl, hexyl, cyclohexyl, a $C_6$–$C_{15}$-aryl group such as phenyl, naphthyl, a $C_1$–$C_{10}$-alkoxy group such as methoxy, ethoxy, tert-butoxy, a $C_6$–$C_{15}$-aryloxy group, a benzyl group, preferably a chlorine atom, a fluorine atom, a methyl group, a benzyl group, particularly preferably a chlorine atom or a methyl group.

Particularly preferred novel metallocenes of the formula (I) have the formula (I*), (I*)

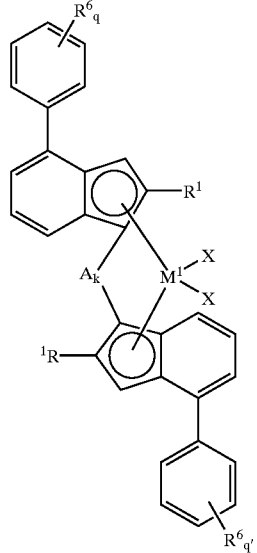

where $M^1$, A, $R^1$, k and X are as defined in formula (I) and $R^6$ are identical or different and are each a hydrogen atom or a $C_1$–$C_{40}$ group, preferably a $C_1$–$C_{20}$-alkyl group which may be substituted, in particular methyl, ethyl, trifluoromethyl, trifluoroethyl, n-propyl, isopropyl, n-butyl, sec-butyl, isobutyl, tert-butyl, pentyl, hexyl, octyl, cyclopropyl, cyclopentyl, cyclohexyl, a $C_6$–$C_{14}$-aryl group which may be substituted, e.g. phenyl, a $C_2$–$C_{20}$-alkynyl group, a $C_7$–$C_{20}$-alkylaryl group, halogen, an $OR^4$ group, an $SiR^4_3$ group, an $NR^4_2$ group, an $SR^4$ group, and two radicals $R^4$ and $R^6$ may each or together form a monocyclic or polycyclic ring system which may in turn be substituted, where $R^4$ is as defined in formula (I) and at least one of the radicals $R^6$ bears or is a cationic group (—$DE_L$)$^+Y^-$, where D, E, L and Y are as defined in formula (I), q is an integer less than or equal to 5 and greater than or equal to 1, preferably 1 or 2, particularly preferably 1, and q' is an integer less than or equal to 5 and greater than or equal to 1, preferably 1 or 2, particularly preferably 1.

Illustrative but nonrestrictive examples of novel metallocenes of the formula (I) are:

dimethylsilanediylbis(2-methyl-4-(4'-trimethylammoniumphenyl)indenyl)dichlorozirconium diiodide dimethylsilanediylbis(2-methyl-4-(4'-trimethylammoniumphenyl)indenyl)dichlorotitanium diiodide dimethylsilanediylbis(2-methyl-4-(4'-trimethylammoniumphenyl)indenyl)dichlorohafnium diiodide dimethylsilanediylbis(2-methyl-4-(3'-trimethylammoniumphenyl)indenyl)dichlorozirconium diiodide dimethylsilanediylbis(2-methyl-4-(2'-trimethylammoniumphenyl)indenyl)dichlorozirconium diiodide dimethylsilanediylbis(2-methyl-4-(3',5'-bis(trimethylammonium)phenyl)indenyl)-dichlorozirconium tetraiodide dimethylsilanediylbis(2-methyl-4-(4'-trimethylammoniumnaphthyl)indenyl)dichlorozirconium diiodide dimethylsilanediylbis(2-methyl-4-(4'-trimethylammoniumphenyl)indenyl)dichlorozirconium ditosylate dimethylsilanediylbis(2-ethyl-4-(4'-trimethylammoniumphenyl)indenyl)dichlorozirconium ditriflate dimethylsilanediylbis(2-methyl-4-(4'-dimethylammoniumphenyl)indenyl)dichlorozirconium dichloride dimethylsilanediylbis(2-methyl-4-(4'-trimethylammoniumphenyl)indenyl)dichlorozirconium bistetrafluoroborate dimethylsilanediylbis(2-methyl-4-(4'-N-methyl-N-pyrrolidinophenyl)indenyl)-dichlorozirconium diiodide dimethylsilanediylbis(2-methyl-4-(4'-dimethylammoniumphenyl)indenyl)dichlorotitanium dichloride dimethylsilanediylbis(2-methyl-4-(4'-dimethyl(methoxymethyl)ammoniumphenyl)-indenyl)dichlorozirconium dichloride dimethylsilanediylbis(2-methyl-4-(4'-dimethyl (2"-methoxyethoxymethyl)-ammoniumphenyl)indenyl)dichlorozirconium dichloride dimethylsilanediylbis(2-methyl-4-(4'-dimethyl(benzyloxymethyl)ammoniumphenyl)-indenyl)dichlorozirconium dichloride dimethylsilanediylbis(2-methyl-4-(4'-dimethyl(2"-trimethylsilylethoxymethyl)-ammoniumphenyl)indenyl)dichlorohafnium dichloride dimethylsilanediylbis(2-methyl-4-(4'-dimethylbenzylammoniumphenyl)indenyl)-dichlorozirconium dichloride dimethylsilanediylbis(2-methyl-4-(4'-dimethylallylammoniumphenyl)indenyl)dichlorozirconium diiodide dimethylsilanediylbis(2-methyl-4-(4'-triethylammoniumphenyl)indenyl)dichlorozirconium diiodide dimethylsilanediylbis(2-ethyl-4-(4'-dimethyl (2"-trimethylsilylethoxymethyl)ammoniumphenyl)indenyl)dichlorohafnium dichloride dimethylsilanediylbis(2-ethyl-4-(4'-dimethylbenzylammoniumphenyl)indenyl)dichlorozirconium dichloride dimethylsilanediylbis(2-ethyl-4-(4'-dimethylallylammoniumphenyl)indenyl)dichlorozirconium diiodide dimethylsilanediylbis(2-ethyl-4-(4'-trimethylammoniumphenyl)indenyl)dichlorozirconium diiodide dimethylsilanediylbis(2-n-butyl-4-(4'-trimethylammoniumphenyl)indenyl)dichlorozirconium diiodide dimethylsilanediylbis(2-isopropyl-4-(4'-triethylammoniumphenyl)indenyl)dichlorozirconium dibromide dimethylsilanediylbis(2-isobutyl-4-(4'-triethylammoniumphenyl)indenyl)dichlorozirconium ditriflate dimethylsilanediylbis(2-ethyl-4-(4'-triethylphosphoniumphenyl)indenyl)dichlorozirconium diiodide dimethylsilanediylbis(2-methyl-4-(4'-dimethylsulfoniumphenyl)indenyl)dichlorozirconium dibromide dimethylsilanediylbis(2-ethyl-4-(4'-dimethylsulfoniumphenyl)indenyl)dichlorozirconium dibromide dimethylsilanediylbis(2-methyl-4-(3'-dimethylsulfoniumphenyl)indenyl)dichlorozirconium dibromide dimethylsilanediylbis(2-methyl-4-(2'-dimethylsulfoniumphenyl)indenyl)dichlorozirconium dibromide dimethylsilanediylbis(2-methyl-4-(3',5'-bis(dimethylsulfonium)phenyl)indenyl)dichlorozirconium tetrabromide dimethylsilanediylbis(2-methyl-4-(4'-dibenzylsulfoniumphenyl)indenyl)dichlorozirconium dibromide dimethylsilanediylbis(2-methyl-4-(4'-methyl(methoxymethyl)sulfoniumphenyl)indenyl)dichlorozirconium dichloride dimethylsilanediylbis(2-methyl-4-(4'-diallylsulfoniumphenyl)indenyl)dichlorozirconium dibromide dimethylsilanediylbis(2-methyl-4-(3'-diphenylethylphosphoniumphenyl)indenyl)dichlorozirconium diiodide dimethylsilanediylbis(2-methyl-4-(3'-trimethylphosphoniumphenyl)indenyl)dichlorozirconium ditriflate methylphenylsilanediylbis(2-isobutyl-4-(4'-triethylammoniumphenyl)indenyl)-dichlorozirconium ditosylate 1,2-ethanediylbis(2-methyl-4-(3'-dimethylammoniumphenyl)indenyl)dichlorozirconium bistrifluoroacetate 1,2-ethanediylbis(2-methyl-4-(4'-dimethylsulfoniumphenyl)indenyl)dichlorozirconium dibromide 1,2-ethanediylbis(2-methyl-4-(3'-diphenylethylphosphoniumphenyl)indenyl)dichlorozirconium diiodide dimethylsilanediylbis(2-methyl-5-trimethylammoniumindenyl)dichlorozirconium dichloride dimethylsilanediylbis(2-methyl-5-trimethylphosphoniumindenyl)dichlorozirconium dichloride 1,2-ethanediylbis(2-methyl-4-dimethylbenzylammoniumindenyl)dichlorozirconium dibromide 1,2-ethanediylbis(2-methyl-4-phenyl-5-dimethylbenzylammoniumindenyl)dichlorozirconium dibromide dimethylsilanediylbis(2-methyl-4-phenyl-6-trimethylammoniumindenyl)dichlorozirconium dichloride dimethylsilanediylbis(2-methyl-5-dimethylsulfoniumindenyl)dichlorozirconium dibromide dimethylsilanediylbis(2-methyl-4-(4'-(2"-trimethylammoniumethyl)phenylindenyl)dichlorozirconium dichloride dimethylsilanediylbis(2-methyl-4-(4'-(3"-dimethylsulfoniumpropyl)phenylindenyl)dichiorozirconium diiodide dimethylsilanediylbis(2-methyl-4-(3'-(2"-trimethylammoniumethyl)phenylindenyl)dichlorozirconium dichloride dimethylsilanediylbis(2-methyl-4-(2"-trimethylammoniumethyl)indenyl)dichlorozirconium dichloride dimethylsilanediylbis(2-(2'-trimethylammoniumethyl)indenyl)dichlorozirconiumdichloride dimethylsilanediylbis(2-(2'-trimethylammbniumethyl)-4-phenylindenyl)dichlorozirconium dibromide dimethylsilanediylbis(2-(2'-dimethylsulfoniumethyl)-4,6-dimethylindenyl)dichlorozirconium diiodide.

The present invention further provides a process for preparing metallocenes of the formula (I). The process of the present invention comprises reacting a metallocene of the formula (Ia) with a reagent EY to give a metallocene of the formula (I).

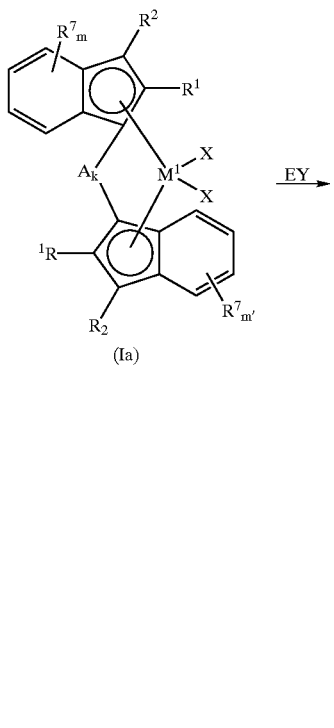

(Ia)

(I)

The radicals $R^1$, $R^2$, $R^3$, A, $M^1$, X, E, Y, k, m and m' are as defined in formula (I), and $R^7$ are identical or different and are each a hydrogen atom or a $C_1$–$C_{40}$ group, preferably a $C_1$–$C_{20}$-alkyl group which may be substituted, in particular methyl, ethyl, trifluoroethyl, n-propyl, isopropyl, n-butyl, sec-butyl, isobutyl, tert-butyl, pentyl, hexyl, octyl, cyclopropyl, cyclopentyl, cyclohexyl, a $C_6$–$C_{14}$-aryl group which may be substituted, in particular phenyl, tolyl, xylyl, tert-butylphenyl, ethylphenyl, trifluoromethylphenyl, bis(trifluoromethyl)phenyl, methoxyphenyl, fluorophenyl, dimethylaminophenyl, methylthiophenyl, diethylphosphinophenyl, naphthyl, acenaphthyl, phenanthrenyl, anthracenyl, a $C_2$–$C_{20}$-alkenyl group, a $C_2$–$C_{20}$-alkynyl group, a $C_7$–$C_{20}$-alkylaryl group, a halogen atom, an SiMe$_3$ group, an OSiMe$_3$ group, a $C_1$–$C_{20}$-heterocyclic group which may be substituted, where the term heteroatom encompasses all elements with the exception of carbon and hydrogen and preferably refers to atoms of groups 14, 15 and 16 of the Periodic Table of the Elements, and two radicals $R^7$ may form a monocyclic or polycyclic ring system which may in turn be substituted.

The metallocene of the formula (Ia) bears a group DEL1 on at least one of the radicals $R^1$, $R^2$, $R^7$, where D is an atom of group 15 or 16 of the Periodic Table of the Elements, in particular nitrogen, phosphorus, oxygen or sulfur, and E and L are as defined in formula (I).

The preparation of metallocenes of the formula (Ia) is carried out by methods known from the literature (e.g. EP-A-0,576,970; Chem. Lett., 1991, 11, p.2047 ff; Journal of Organometallic Chem., 288 (1985) 63–67 and documents cited therein).

The reagent EY is a compound capable of transferring the radical E, where E and Y are as defined in formula (I).

Illustrative but nonrestrictive examples of the reagent EY are:

methyl iodide, methyl bromide, methyl chloride, methyl triflate, methyl trifluoroacetate, methyl methanesulfonate, methyl p-toluenesulfonate, dimethyl sulfate, trimethyloxonium tetrafluoroborate, trimethyloxonium hexafluorophosphate, ethyl iodide, ethyl bromide, ethyl chloride, triethyloxonium tetrafluoroborate, triethyloxonium hexafluorophosphate, propyl iodide, propyl bromide, propyl triflate, butyl bromide, butyl iodide, butyl chloride, pentyl bromide, octyl bromide, benzyl chloride, benzyl bromide, benzyl triflate, allyl bromide, allyl chloride, p-methoxybenzyl chloride, trimethylsilyl chloride, trimethylsilyl bromide, trimethylsilyl iodide, timethylsilyl triflate, tert-butyldimethylsilyl chloride, tert-butyldimethylsilyl triflate; triphenylsilyl chloride, triphenylsilyl iodide, triphenylsilyl triflate, methoxymethyl chloride (MOMCl), 2-methoxyethoxymethyl chloride (MEMCl), 2-trimethylsilylethoxymethyl chloride (SEMCl), benzyloxymethyl chloride (BOMCl), hydrogen fluoride, hydrogen chloride, hydrogen bromide, hydrogen iodide, trifluoroacetic acid, methanesulfonic acid, trifluoromethanesulfonic acid, p-toluenesulfonic acid, sulfuric acid, perchloric acid, acetic acid, triethylamine hydrochloride, trimethylamine hydrofluoride, tetrafluoroboric acid diethyl etherate, hexafluorophosphoric acid.

The process of the present invention can be carried out in the presence of a suitable solvent or in bulk. Nonrestrictive examples of suitable solvents are hydrocarbons which may be halogenated, for example benzene, toluene, xylene, mesitylene, ethylbenzene, chlorobenzene, dichlorobenzene, fluorobenzene, decalin, pentane, hexane, cyclohexane, dichloromethane, chloroform, tetrachloromethane, 1,2-dichloroethane, trichloroethylene, ethers such as diethyl ether, di-n-butyl ether, MTBE, THF, DME, anisole, triglyme, dioxane, amides such as DMF, dimethylacetamide, NMP, sulfoxides such as DMSO, phosphoramides such as hexamethylphosphoramide, urea derivatives such as DMPU, ketones such as acetone, ethyl methyl ketone, esters such as ethyl acetate, nitriles such as acetonitrile and also any mixtures of these substances.

The process of the present invention is generally carried out in a temperature range from −100° C. to +500° C., preferably in a temperature range from −78° C. to +200° C., particularly preferably at from 0° C. to 100° C.

The reaction can be carried out in a single-phase system or in a multiphase system.

The molar ratio of reagent EY to metallocene (Ia) is generally in the range from 0.5 to 100, preferably from 1 to 10.

The concentration of metallocene (Ia) or of reagent EY in the reaction mixture is generally in the range from 0.001 mol/l to 8 ml/l, preferably in the range from 0.01 to 3 mol/l, particularly preferably in the range from 0.1 mol/l to 2 mol/l.

The reaction time for the reaction of metallocenes of the formula (Ia) with a reagent EY is generally in the range from 5 minutes to 1 week, preferably in the range from 15 minutes to 48 hours.

The compounds of the present invention are particularly suitable as constituents of catalyst systems for the polymerization of olefins based on ethylene, propylene, norbornadiene and also of functionalized olefins, with both homopolymers and copolymers being obtainable.

The invention is illustrated by the following nonrestrictive examples.

General information: preparation and handling of the organometallic compounds was carried out under argon with exclusion of air and moisture (Schlenk technique or glove box). All solvents required were purged with argon and dried over molecular sieves before use.

EXAMPLE 1

Dimethylsilanediylbis(2-methyl-4-(4'-trimethylammoniumphenyl)indenyl) dichlorozirconium diiodide (1)

4.5 g (0.02 mol) of 2-methyl-7-bromo-1-indanone, 3.63 g (0.022 mol) of 4-N,N-dimethylaminophenylboronic acid and 4.66 g (0.044 mol) of sodium carbonate were added to a mixture of 80 ml of 1,2-dimethoxyethane and 25 ml of water, and the resulting mixture was degassed and saturated with argon a number of times. 90 mg (0.4 mmol) of palladium acetate and 0.2 g (0.8 mmol) of triphenylphosphine were added and the reaction mixture was stirred at 80° C. for 3 hours. After addition of 100 ml of water, the mixture was extracted with diethyl ether and the combined organic phases were washed with water and dried over magnesium sulfate. Removal of the solvent and column filtration through neutral aluminum oxide (dichloromethane) gave 5.1 g of 2-methyl-7-(4'-N,N-dimethylaminophenyl)-1-indanone.

$^1$H-NMR (300 MHz, CDCl$_3$): 7.58–7.24 (m, 5H), 6.78 (d, 2H), 3.38 (m, 1H), 3.01(6H), 2.78–2.65 (m, 2H), 1.28 (d, 2H).

760 mg (20 mmol) of sodium borohydride were added at 0° C. to a solution of 5.0 g (0.019 mol) of 2-methyl-7-(4'-N,N-dimethylaminophenyl)-1-indanone in 100 ml of THF/methanol (2:1) and the mixture was stirred at room temperature (20° C.) for 18 hours. The reaction mixture was poured into ice water, admixed with concentrated hydrochloric acid until the pH was 1, then brought to pH 9 using 2 M sodium hydroxide solution and extracted a number of times with dichloromethane. The combined organic phases were washed with water and with sodium chloride solution and dried over magnesium sulfate. Removal of the solvent gave the crude product 2-methyl-7-(4'-N,N-dimethylaminophenyl)-1-indanol, which was taken up in 100 ml of toluene. After addition of 3.1 g (0.027 mol) of trifluoroacetic acid, the mixture was stirred at 100° C. for 2 hours. It was subsequently admixed with 2 M sodium hydroxide solution until the pH was 9, the phases were separated and the solvent was removed. 4.6 g of 2-methyl-4-(4'-N,N-dimethylaminophenyl)indene were isolated.

$^1$H-NMR (300 MHz, CDCl$_3$): 7.46–7.21 (m, 5H), 6.86–6.81 (m, 2H), 6.72 (s, 1H), 3.36 (s, 2H), 3.05 (s, 6H), 2.15 (s, 3H).

A solution of 10.0 g (40.2 mmol) of 2-methyl-4-(4'-N,N-dimethylaminophenyl)indene in 100 ml of toluene and 5 ml of THF was admixed at room temperature with 16.7 ml (44 mmol) of a 20% solution of butyllithium in toluene and heated at 80° C. for 2 hours. The suspension was subsequently cooled to 0° C. and admixed with 2.76 g (21 mmol) of methyldichlorosilane. The reaction was heated at 80° C. for a further 1 hour and subsequently washed with 50 ml of water. The solvent was removed under reduced pressure and the residue was recrystallized from heptane at −20° C. This gave 7.8 g of ligand as colorless crystals.

5.0 g (9 mmol) of the ligand were dissolved in 70 ml of diethyl ether, admixed at room temperature with 6.84 ml (18 mmol) of a 20% strength solution of butyllithium in toluene and subsequently refluxed for 3 hours. The solvent was removed under reduced pressure and the residue was taken up in 50 ml of hexane and filtered through a G3 Schlenk frit, washed with 50 ml of hexane and dried (0.1 mbar, 20° C.). The dilithium salt was added at −78° C. to a suspension of 2.2 g (9.5 mmol) of zirconium tetrachloride in 50 ml of methylene chloride and warmed to room temperature over a period of 18 hours while stirring. The mixture was filtered through a G3 frit and the residue was extracted a number of times with methylene chloride, using a total of 400 ml of methylene chloride. The combined filtrates were largely freed of solvent under reduced pressure. The crystalline precipitate which separated out from methylene chloride was separated off. This gave 3.8 g of metallocene as a mixture of racemic and meso forms in a ratio of 1:1. This product was recrystallized again from methylene chloride to give 1.4 of the racemic complex in the form of yellow crystals.

$^1$H-NMR (300 MHz, CDCl$_3$): 7.62–7.00 (m, 10H), 6.88–6.76 (m, 6H), 2.95 (s, 12), 2.42 (s, 6H), 1.18 (s, 6H).

1.0 g(1.4 mmol) of dimethylsilanediylbis(2-methyl-4-(4'-(N,N-dimethylaminophenyl)indenyl)zirconium dichloride was dissolved in a mixture of 15 ml of toluene and 15 ml of THF, and the solution was admixed with 7.95 g (5.6 mmol) of methyl iodide and stirred for three hours at 45° C. The reaction mixture was subsequently evaporated to dryness and the residue was washed with a little toluene and pentane, giving 1.29 g of dimethylsilanediylbis(2-methyl-4-(4'-trimethylammoniumphenyl)indenyl)dichlorozirconium diiodide (1) as a yellow-orange solid.

$^1$H-NMR (300 MHz, DMSO-d6): 7.70–7.05 (m, 10H), 6.89–6.79 (m, 6H), 3.51 (s, 18H), 2.49 (s, 6H), 1.21 (s, 6H).

EXAMPLE 2

Dimethylsilanediylbis(2-methyl-4-(4'-dimethylsulfoniumphenyl)indenyl) dichlorozirconium dibromide [2]

The preparation of dimethylsilanediylbis(2-methyl-4-(4'-methylthiophenyl)indenyl)zirconium dichloride was carried out in a manner analogous to EXAMPLE 1. It was subsequently reacted with methyl bromide using a method analogous to Example 1 to give [2].

EXAMPLE 3

Dimethylsilanediylbis(2-methyl-4-(3'-diphenylethylphosphoniumphenyl)indenyl) dichlorozirconium diiodide [3]

The preparation of dimethylsilanediylbis(2-methyl-4-(3'-diphenylphosphinophenyl)indenyl)zirconium dichloride was carried out in a manner analogous to Example 1. It was subsequently reacted with ethyl iodide using a method analogous to Example 1 to give [3].

EXAMPLE 4

Dimethylsilanediylbis(2-methyl-4-(4'-dimethylammoniumphenyl)indenyl) dichlorozirconium dichloride [4]

The preparation of dimethylsilanediylbis(2-methyl-4-(4'-dimethylaminophenyl)indenyl)zirconium dichloride was carried out in a manner analogous to Example 1. It was subsequently reacted at 0° C. with two equivalents of hydrogen chloride solution in THF to give [4].

EXAMPLE 5

Dimethylsilanediylbis(2-methyl-4-(4'-dimethyl(methoxymethyl)ammoniumphenyl)indenyl) dichlorozirconium dichloride [5]

The preparation of dimethylsilanediylbis(2-methyl-4-(4'-dimethyl(methoxymethyl)ammoniumphenyl)indenyl)

zirconium dichloride was carried out in a manner analogous to Example 1. It was subsequently reacted with methoxymethyl chloride (MOMCl) using a method analogous to Example 1 to give [5].

EXAMPLE 6

1,2-Ethanediylbis(2-methyl-4-(3'-dimethylammoniumphenyl)indenyl)dichlorozirconium bistrifluoroacetate [6]

The preparation of dimethylsilanediylbis(2-methyl-4-(3'-dimethylammoniumphenyl)indenyl)zirconium dichloride was carried out in a manner analogous to Example 1 using 1,2-dibromoethane in the ligand synthesis. This was subsequently reacted at 0° C. with two equivalents of trifluoroacetic acid to give [6].

EXAMPLE 7

Dimethylsilanediylbis(2-methyl-4-(4'-dimethyl(2''-trimethylsilylethoxymethyl)ammoniumphenyl)indenyl)dichlorohafnium dichloride [7]

The preparation of dimethylsilanediylbis(2-methyl-4-(4'-dimethyl(2''-trimethylsilylethoxymethyl)ammoniumphenyl)indenyl)hafnium dichloride was carried out in a manner analogous to Example 1 using hafnium tetrachloride in the synthesis of the complex. This was subsequently reacted with 2-trimethylsilylethoxymethyl chloride (SEMCl) using a method analogous to Example 1 to give [7].

We claim:

1. A compound of the formula (I)

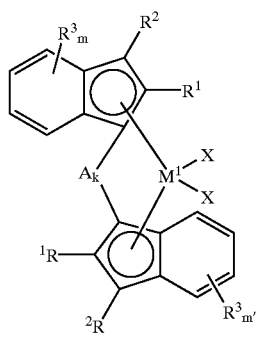

(I)

where

M$^1$ is a transition metal of group 4 of the Periodic Table of the Elements,

R$^1$ and R$^2$ are identical or different and are each a hydrogen atom, a halogen atom or a C$_1$–C$_{20}$ group, R3 are identical or different and are each a hydrogen atom, a halogen atom or a C$_1$–C$_{40}$ group, and two radicals R$^3$ may form a monocyclic or polycyclic ring system which may in turn be substituted, where at least one of the radicals R$^3$ comprises a cationic group (—DE$_L$)$^+$Y$^-$ where D is an atom of group 15 or 16 of the Periodic Table of the Elements, E are identical or different and are each a hydrogen atom or a C$_1$–C$_{20}$ group, and two radicals E may form a monocyclic or polycyclic ring system which may in turn be substituted, L is 3 when D is an atom of group 15 of the Periodic Table of the Elements and is 2 when D is an atom of group 16 of the Periodic Table of the Elements, Y is halogen C$_1$–C$_{10}$-alkylsulfonate, C$_1$–C$_{10}$-haloalkylsulfonate, C$_6$–C$_{20}$-alkylsulfonate, C$_6$–C$_{20}$-haloarylsulfonate, C$_1$–C$_{20}$-alkylarylsulfonate, C$_1$–C$_{20}$-haloalkylcarboxylate, C$_1$–C$_{10}$-alkyl sulfate, tetrafluoroborate, hexafluorophosphate, hexafluoroantimonate or hexafluoroarsenate, m is an integer less than or equal to 4 and greater than or equal to 1, m' is an integer smaller than or equal to 4 and greater than or equal to 1, k is zero or 1, where the metallocene is unbridged when k=0 and is bridged when k=1, A is a bridge of the formula

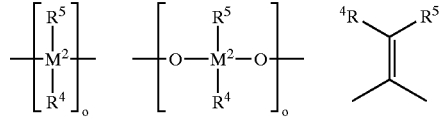

or =BR$^4$, AlR$^4$, —S—, —SO—, —SO$_2$—, =NR$^4$, =PR$^4$, =P(O)R$^4$, o-phenylene, 2,2'-biphenylene, where M$^2$ is Carbon, silicon, germanium, tin, nitrogen or phosphorus, o is 1, 2, 3 or 4, R$^4$ and R$^5$ are identical or different and are each a hydrogen atom, halogen or a C$_1$–C$_{20}$ group, and R$^4$ and R$^5$ may form a monocyclic or polycyclic ring system.

2. A compound as claimed in claim 1, wherein, in formula (I),

M$^1$ is titanium, zirconium or hafnium,

R$^1$ and R$^2$ are identical or different and are each a hydrogen atom, a C$_1$–C$_{20}$-alkyl group, a C$_6$–C$_{14}$-aryl group, a C$_2$–C$_{20}$-alkenyl group, a C$_2$–C$_{20}$-alkynyl group, a C$_7$–C$_{20}$-alkylaryl group which may bear one or more identical or different halogen atoms as substituents, a halogen atom, an —SiMe$_3$ group or an OSiMe$_3$ group, R3 are identical or different and are each a hydrogen atom, a C$_1$–C$_{20}$-alkyl group which may be substituted, a C$_6$–C$_{14}$-aryl group which may be substituted, a C$_2$–C$_{20}$-alkenyl group, a C$_2$–C$_{20}$-alkynyl group, a C$_7$–C$_{20}$-alkylaryl group, a halogen atom, an SiMe$_3$ group, an OSiMe$_3$ group, a C$_1$–C$_{20}$-heterocyclic group, each of which may be substituted, where the term hetero atom encompasses all elements with the exception of carbon and hydrogen and preferably refers to atoms of groups 14, 15 and 16 of the Periodic Table of the Elements, and two radicals R$^3$ may form a monocyclic or polycyclic ring system which may in turn be substituted, where at least one of the radicals R$^3$ comprises a cationic group (—DE$_L$)$^+$Y$^-$ where D is nitrogen, phosphorus, oxygen or sulfur, E are identical or different and are each a hydrogen atom, a C$_1$–C$_{20}$-alkyl group, a C$_6$–C$_{14}$-aryl group, a C$_2$–C$_{20}$-alkenyl group, a C$_2$–C$_{20}$-alkynyl group, a C$_7$–C$_{20}$-alkylaryl group, a trialkylsilyl group, a triarylsilyl group, an alkylarylsilyl group, each of which may be substituted, and two radicals E may form a monocyclic or polycyclic ring system which may in turn be substituted, L is 3 when D is an atom of group 15 of the Periodic Table of the Elements and is 2 when D is an atom of group 16 of the Periodic Table of the Elements, Y is chloride, bromide, iodide, triflate, mesylate, tosylate, benzenesulfonate, trifluoroacetate, methyl sulfate, tetrafluoroborate or hexafluorophosphate, m is 1 or 2, m' is 1 or 2, k is zero or 1, where the metallocene is unbridged when k=0 and is bridged when k=1, A is a bridge of the formula

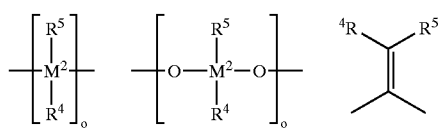

or $=BR^4$, $AlR^4$, —S—, —SO—, —$SO_2$—, $=NR^4$, $=PR^4$, $=P(O)R^4$, o-phenylene, 2,2'-biphenylene, where $M^2$ is carbon, silicon or germanium, o is 1 or 2, $R^4$ and $R^5$ are identical or different and are each a hydrogen atom, halogen, a $C_1$–$C_{20}$-alkyl group, a $C_6$–$C_{14}$-aryl group, a $C_1$–$C_{10}$-alkoxy group, a $C_2$–$C_{20}$-alkenyl group, a $C_7$–$C_{20}$-arylalkyl group, a $C_7$–$C_{20}$-alkylaryl group, a $C_6$–$C_{10}$-aryloxy group, a $C_1$–$C_{10}$-fluoroalkyl group, a $C_6$–$C_{10}$-haloaryl group, a $C_2$–$C_{10}$-alkynyl group, a $C_3$–$C_{20}$-alkylsilyl group, a $C_3$–$C_{20}$-arylsilyl group or a $C_3$–$C_{20}$-alkylarylsilyl group, and $R^4$ and $R^5$ may form a monocyclic or polycyclic ring system.

3. A compound as claimed in claim 1, wherein, in formula (I), $M^1$ is zirconium, $R^1$ and $R^2$ are identical or different and are each a hydrogen atom, methyl, ethyl, n-propyl, isopropyl, n-butyl, sec-butyl, isobutyl, tert-butyl, n-pentyl, branched pentyl, n-hexyl, branched hexyl, cyclohexyl or benzyl, $R^3$ are identical or different and are each a hydrogen atom, methyl, ethyl, trifluoroethyl, n-propyl, isopropyl, n-butyl, sec-butyl, isobutyl, tert-butyl, pentyl, hexyl, octyl, cyclopropyl, cyclopentyl, cyclohexyl, phenyl, tolyl, xylyl, tert-butylphenyl, ethylphenyl, trifluoromethylphenyl, bis(trifluoromethyl)phenyl, methoxyphenyl, fluorophenyl, dimethylaminophenyl, trimethylammoniumphenyl iodide, dimethylsulfoniumphenyl bromide, triethylphosphoniumphenyl triflate, naphthyl, acenaphthyl, phenanthrenyl, anthracenyl, a $C_1$–$C_{20}$-heterocyclic group which may be substituted, where the term hetero atom encompasses all elements with the exception of carbon and hydrogen and preferably refers to atoms of groups 14, 15 and 16 of the Periodic Table of the Elements, and two radicals $R^3$ may form a monocyclic or polycyclic ring system which may in turn be substituted, where the radicals $R^3$ comprises a cationic group $(-DE_L)^+Y^-$ where D is nitrogen, phosphorous or sulfur, E are identical or different and are each a hydrogen atom, methyl, ethyl, propyl, butyl, allyl, benzyl, methoxymethyl, benzyloxymethyl, 2-methoxyethoxymethyl, 2-trimethylsilylethoxymethyl or trimethylsilyl, L is 3 when D is an atom of group 15 of the Periodic Table of the Elements and is 2 when D is an atom of group 16 of the Periodic Table of the Elements, Y is chloride, bromide, iodide, triflate, mesylate, tosylate, benzenesulfonate, trifluoroacetate, methyl sulfate, tetrafluoroborate or hexafluorophosphate, m is 1, m' is 1, k is zero or 1, where the metallocene is unbridged when k=0 and is bridged when k=1, A is a bridge of the formula

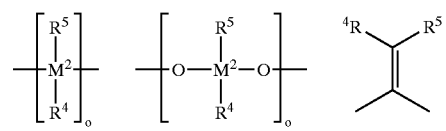

or $=BR^4$, $AlR^4$, —S—, —SO—, —$SO_2$—, $=NR^4$, $=PR^4$, $=P(O)R^4$, o-phenylene, 2,2'-biphenylene, where $M^2$ is carbon or silicon, o is 1 or 2, $R^4$ and $R^5$ are identical or different and are each a hydrogen atom, halogen, methyl, phenyl or naphthyl, trimethylsilyl, triethylsilyl, tert-butyldimethylsilyl, triphenylsilyl, dimethylphenylsilyl, diphenylsilyl or diphenyl-tert-butylsilyl and $R^4$ and $R^5$ may form a monocyclic or polycyclic ring system.

4. A compound as claimed in claim 1, wherein, in formula (I), A is dimethylsilanediyl, dimethylgermanediyl, ethylidene, methylethylidene, 1,1-dimethylethylidene, 1,2-dimethylethylidene, tetramethylethylidene, isopropylidene, phenylmethylmethylidene or diphenylmethylidene.

5. A compound as claimed in claim 1, wherein the metallocene has the formula (I*),

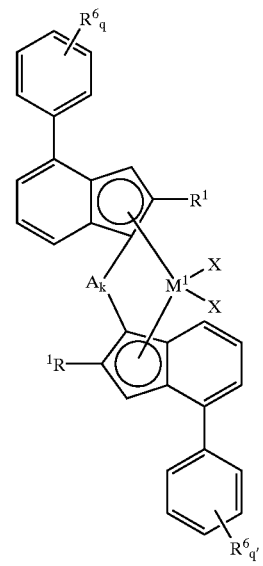

(I*)

where $M^1$, A, $R^1$, k and X are as defined in formula (I) and $R^6$ are identical or different and are each a hydrogen atom, a $C_1$–$C_{20}$-alkyl group which may be substituted, a $C_6$–$C_{14}$-aryl group which may be substituted, a $C_2$–$C_{20}$-alkynyl group, a $C_7$–$C_{20}$-alkylaryl group, halogen, an $OR^4$ group, an $SiR^4_3$ group, an $NR^4_2$ group, an $SR^4$ group, and two radicals $R^4$ and $R^6$, each or together, may form a monocyclic or polycyclic ring system which may in turn be substituted, where $R^4$ is as defined in formula (I) and at least one of the radicals $R^6$ bears a cationic group $(-DE_L)^+Y^-$, where D, E, L and Y are as defined in formula (I), q is an integer less than or equal to 5 and greater than or equal to 1, q' is an integer less than or equal to 5 and greater than or equal to 1.

6. A compound as claimed in claim 5, wherein, in formula (I*), $R^6$ are identical or different and are each a hydrogen atom, methyl, ethyl, trifluoromethyl, trifluoroethyl, n-propyl, isopropyl, n-butyl, sec-butyl, isobutyl, tert-butyl, pentyl, hexyl, octyl, cyclopropyl, cyclopentyl, cyclohexyl, phenyl, and at least one of the radicals $R^6$ bears a cationic group $(-DE_L)^+Y^-$, where D, E, L and Y are as defined in formula (I), q is 1 or 2, q' is 1 or 2.

7. A compound as claimed in claim 1, wherein the formula (I) represents dimethylsilanediylbis(2-methyl-4-(4'-trimethylammonium phenyl)indenyl)dichlorozirconium diiodide dimethylsilanediylbis(2-methyl-4-(4'-trimethylammonium phenyl)indenyl)dichlorotitanium diiodide dimethylsilanediylbis(2-methyl-4-(4'-trimethylammoniumphenyl)indenyl)dichlorohafnium diiodide dimethylsilanediylbis(2-methyl-4-(3'-trimethylammoniumphenyl)indenyl)dichlorozirconium diiodide dimethylsilanediylbis(2-methyl-4-(2'-tdmethylammoniumphenyl)indenyl)dichlorozirconium diiodide dimethylsilanediylbis(2-methyl-4-(3',5'-bis(trimethylammonium)phenyl)indenyl)dichlorozirconium tetraiodide dimethylsilanediylbis(2-methyl-4-(4'-trimethylammoniumnaphthyl)indenyl)dichlorozirconium diiodide dimethylsilanediylbis(2-methyl-4-(4'-trimethylammoniumphenyl)indenyl)dichlorozirconium ditosylate dimethylsilanediylbis(2-ethyl-4-(4'-trimethylammoniumphenyl)indenyl)dichlorozirconium ditriflate dimethylsilanediylbis(2-methyl-4-(4'-dimethylammoniumphenyl)indenyl)dichlorozirconium dichloride dimethylsilanediylbis(2-methyl-4-(4'-trimethylammoniumphenyl)indenyl)dichlorozirconium bistetrafluoroborate dimethylsilanediylbis(2-methyl-4-(4-N-methyl-N-pyrrolidinophenyl)indenyl)dichlorozirconium diiodide dimethylsilanediylbis(2-methyl-4-(4'-dimethylammoniumphenyl)indenyl)dichlorotitanium dichloride dimethylsilanediylbis(2-methyl-4-(4'-dimethyl(methoxymethyl)ammoniumphenyl)indenyl)dichlorozirconium dichloride dimethylsilanediylbis(2-methyl-4-(4'-dimethyl(2''-methoxyethoxymethyl)ammoniumphenyl)indenyl)dichlorozirconium dichloride dimethylsilanediylbis(2-methyl-4(4'-dimethyl(benzyloxymethyl)ammoniumphenyl)indenyl)dichlorozirconium dichloride dimethylsilanediylbis(2-methyl-4-(4'-dimethyl(2''-trimethylsilylethoxymethyl)ammoniumphenyl)indenyl)dichlorohafnium dichloride dimethylsilanediylbis(2-methyl-4-(4'-dimethylbenzylammoniumphenyl)indenyl)dichlorozirconium dichloride dimethylsilanediylbis(2-methyl-4-(4'-dimethylallylammoniumphenyl)indenyl)dichlorozirconium diiodide dimethylsilanediylbis(2-methyl-4-(4'-triethylammoniumphenyl)indenyl)dichlorozirconium diiodide dimethylsilanediylbis(2-ethyl-4-(4'-dimethyl(2''-trimethylsilylethoxymethyl)-ammoniumphenyl)indenyl)dichlorohafnium dichloride dimethylsilanediylbis(2-ethyl-4-(4'-dimethylbenzylammoniumphenyl)indenyl)dichlorozirconium dichloride dimethylsilanediylbis(2-ethyl-4-(4'-dimethylallylammoniumphenyl)indenyl)dichlorozirconium diiodide dimethylsilanediylbis(2-ethyl-4-(4'-trimethylammoniumphenyl )indenyl)dichlorozirconium diiodide dimethylsilanediylbis(2-n-butyl-4-(4'-trimethylammoniumphenyl)indenyl)dichlorozirconium diiodide dimethylsilanediylbis(2-isopropyl-4-(4'-triethylammoniumphenyl)indenyl)-dichlorozirconium dibromide dimethylsilanediylbis(2-isobutyl-4-(4'-triethylammoniumphenyl)indenyl)dichlorozirconium ditriflate dimethylsilanediylbis(2-ethyl-4-(4'-triethylphosphoniumphenyl)indenyl)dichlorozirconium diiodide dimethylsilanediylbis(2-methyl-4-(4'-dimethylsulfoniumphenyl)indenyl)dichlorozirconium dibromide dimethylsilanediylbis(2-ethyl-4(4'-dimethylsulfoniumphenyl)indenyl)dichlorozirconium dibromide dimethylsilanediylbis(2-methyl-4-(3'-dimethylsulfoniumphenyl)indenyl)dichlorozirconium dibromide dimethylsilanediylbis(2-methyl-4-(2'-dimethylsulfoniumphenyl)indenyl)dichlorozirconium dibromide dimethylsilanediylbis(2-methyl-4-(3',5'-bis(dimethylsulfonium)phenyl)indenyl)dichlorozirconium tetrabromide dimethylsilanediylbis(2-methyl-4-(4'-dibenzylsulfoniumphenyl)indenyl)dichlorozirconium dibromide dimethylsilanediylbis(2-methyl-4-(4'-methyl(methoxymethyl)sulfoniumphenyl)indenyl)dichlorozirconium dichloride dimethylsilanediylbis(2-methyl-4-(4'-diallylsulfoniumphenyl)indenyl)dichlorozirconium dibromide dimethylsilanediylbis(2-methyl-4-(3'-diphenylethylphosphoniumphenyl)indenyl)dichlorozirconium diiodide dimethylsilanediylbis(2-methyl-4-(3'-triethylphosphoniumphenyl)indenyl)dichlorozirconium ditriflate methylphenylsilanediylbis(2-isobutyl-4-(4'-triethylammoniumphenyl)indenyl)dichlorozirconium ditosylate 1,2-ethanediylbis(2-methyl-4-(3'-dimethylammoniumphenyl)indenyl)dichlorozirconium bistrifluoroacetate 1,2-ethanediylbis(2-methyl-4-(4'-dimethylsulfoniumphenyl)indenyl)dichlorozirconium dibromide 1,2-ethanediylbis(2-methyl-4-(3'-diphenylethylphosphoniumphenyl)indenyl)dichlorozirconium diiodide dimethylsilanediylbis(2-methyl-5-trimethylammoniumindenyl)dichlorozirconium dichloride dimethylsilanediylbis(2-methyl-5-trimethylphosphoniumindenyl)dichlorozirconium dichloride 1,2-ethanediylbis(2-methyl-4-dimethylbenzylammoniumindenyl)dichlorozirconium dibromide 1,2-ethanediylbis(2-methyl-4-phenyl-5-dimethylbenzylammoniumindenyl)dichlorozirconium dibromide dimethylsilanediylbis(2-methyl-4-phenyl-6-trimethylammoniumindenyl)dichlorozirconium dichloride dimethylsilanediylbis(2-methyl-5-dimethylsulfoniumindenyl)dichlorozirconium dibromide dimethylsilanediylbis(2-methyl-4-(4'-(2"-trimethylammoniumethyl)phenylindenyl)dichlorozirconium dichloride dimethylsilanediylbis(2-methyl-4-(4'-(3"-dimethylsulfoniumpropyl)phenylindenyl)dichlorozirconium diiodide dimethylsilanediylbis(2-methyl-4-(3'-(2"-trimethylammoniumethyl)phenylindenyl)dichlorozirconium dichloride dimethylsilanediylbis(2-methyl-4-(2'-trimethylammoniumethyl)indenyl)dichloro zirconium dichloride or a mixture thereof.

8. A process for preparing a polyolefin by polymerization of one or more olefins in the presence of a compound of the formula (I) as claimed in claim 1.

\* \* \* \* \*